United States Patent
Yamamoto et al.

(10) Patent No.: US 11,116,793 B2
(45) Date of Patent: Sep. 14, 2021

(54) MODIFIED METAL NANOPARTICLE COMPRISING CYCLIC POLYETHER AND PHARMACEUTICAL COMPOSITION

(71) Applicant: National University Corporation Hokkaido University, Sapporo (JP)

(72) Inventors: Takuya Yamamoto, Sapporo (JP); Jose Enrico Quinsaat, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 52 days.

(21) Appl. No.: 16/188,509

(22) Filed: Nov. 13, 2018

(65) Prior Publication Data

US 2019/0142865 A1 May 16, 2019

(30) Foreign Application Priority Data

Nov. 13, 2017 (JP) .............................. JP2017-218620

(51) Int. Cl.

| B32B 5/16 | (2006.01) |
|---|---|
| A61K 33/38 | (2006.01) |
| A61K 47/69 | (2017.01) |
| A61K 47/59 | (2017.01) |
| A61K 33/242 | (2019.01) |
| A61K 49/00 | (2006.01) |
| A61K 9/14 | (2006.01) |

(52) U.S. Cl.
CPC .............. *A61K 33/38* (2013.01); *A61K 9/141* (2013.01); *A61K 9/145* (2013.01); *A61K 33/242* (2019.01); *A61K 47/59* (2017.08); *A61K 47/6923* (2017.08); *A61K 49/0065* (2013.01); *Y10T 428/2991* (2015.01)

(58) Field of Classification Search
CPC . B82Y 30/00; B82Y 40/00; B22F 1/00; Y10T 428/2991
USPC .................................. 424/489, 490; 428/403
See application file for complete search history.

(56) References Cited

U.S. PATENT DOCUMENTS

| 2011/0182996 A1* | 7/2011 | Fukushima | ............ C08G 71/04 424/490 |
|---|---|---|---|
| 2014/0072901 A1* | 3/2014 | Fuller | ..................... C08F 12/34 429/483 |

FOREIGN PATENT DOCUMENTS

| JP | 2012-532847 A | | 12/2012 |
|---|---|---|---|
| WO | WO 2010/083041 A1 | * | 7/2010 |
| WO | 2011/003999 A1 | | 1/2011 |
| WO | WO 2014/066793 A1 | * | 5/2014 |

OTHER PUBLICATIONS

Ho et al. 15-Crown-5 Functionalized Au Nanoparticles Synthesized via Single Molecule Exchange on Silica Nanoparticles: Its Application to Probe 15-Crown-5/K+/15-Crown-5 "Sandwiches" as Linking Mechanisms, J. Phys. Chem. C2009, 113, 1686-1693 (Year: 2009).*

ZHANG et al., Lead (II) ion detection in surface water with pM sensitivity using aza-crown-ether-modified silver nanoparticles via dynamic light scattering, Nanotechnology 22 (2011) 275504 (8pp) (Year: 2011).*

(Continued)

*Primary Examiner* — Hoa (Holly) Le
(74) *Attorney, Agent, or Firm* — Sughrue Mion, PLLC

(57) ABSTRACT

A modified metal nanoparticle comprising a metal nanoparticle and a cyclic polyether modifying the metal nanoparticle.

20 Claims, 3 Drawing Sheets

(56) References Cited

OTHER PUBLICATIONS

Lin et al., Recognition of Potassium Ion in Water by 15-Crown-5 Functionalized Gold Nanoparticles, Anal. Chem. 2002, 74, 330-335 (Year: 2002).*
Sakai et al, Single-Step Synthesis and Stabilization of Metal Nanoparticles in Aqueous Pluronic Block Copolymer Solutions at Ambient Temperature, Langmuir 2004, 20, 8426-8430 (Year: 2004).*
Sardar et al., Polymer-Induced Synthesis of Stable Gold and Silver Nanoparticles and Subsequent Ligand Exchange in Water, Langmuir 2007, 23, 11883-11889 (Year: 2007).*

* cited by examiner

MODIFIED METAL NANOPARTICLE COMPRISING CYCLIC POLYETHER AND PHARMACEUTICAL COMPOSITION

TECHNICAL FIELD

The present invention relates to a modified metal nanoparticle and a pharmaceutical composition comprising the modified metal nanoparticle.

BACKGROUND

Conventionally, metal nanoparticles have been applied in applications such as biosensors, intracellular probes, drug delivery substances, and optical contrast substances. For example, Patent Literature 1 discloses the use of metal nanoparticles as a pharmaceutical composition used for radiotherapy.

CITATION LIST

Patent Literature

Patent Literature 1 Japanese Unexamined Patent Publication No. 2012-532847

SUMMARY

However, conventional metal nanoparticles are not necessarily sufficient in salt tolerance, and they may degrade or deteriorate in a living body, resulting in failure to obtain a sufficient effect.

It is an object of the present invention to provide a modified metal nanoparticle excellent in salt tolerance and capable of being suitably used as a pharmaceutical composition. It is also an object of the present invention to provide a pharmaceutical composition comprising the modified metal nanoparticle.

One aspect of the present invention relates to a modified metal nanoparticle comprising a metal nanoparticle and a cyclic polyether modifying the metal nanoparticle.

Such a modified metal nanoparticle is excellent in salt tolerance and can be suitably used as a pharmaceutical composition. Further, since the above-mentioned modified metal nanoparticle is also excellent in heat resistance, it can be suitably used particularly for applications, for example, requiring heat resistance, such as therapeutic agents utilizing a photothermal effect.

In one mode, the metal nanoparticle may be a gold nanoparticle or a silver nanoparticle.

In one mode, the average particle size of the metal nanoparticle may be 1 to 1000 nm.

In one mode, the cyclic polyether may be a cyclic polyethylene oxide.

In one mode, the number average molecular weight of the cyclic polyether may be 500 to 20000.

In one mode, the metal nanoparticle may be a gold nanoparticle and the mass ratio of the cyclic polyether to the gold nanoparticle may be 50 to 1500.

In one mode, the metal nanoparticle may be a silver nanoparticle and the mass ratio of the cyclic polyether to the silver nanoparticle may be 0.1 to 50.

Another aspect of the present invention relates to a pharmaceutical composition comprising the modified metal nanoparticle.

The pharmaceutical composition according to one mode may be a radiosensitizer, a photothermal therapeutic agent, or an MRI contrast agent.

According to the present invention, there is provided a modified metal nanoparticle excellent in salt tolerance and capable of being suitably used as a pharmaceutical composition. Further, according to the present invention, there is a provided a pharmaceutical composition comprising the modified metal nanoparticle.

DETAILED DESCRIPTION

Figure 1:
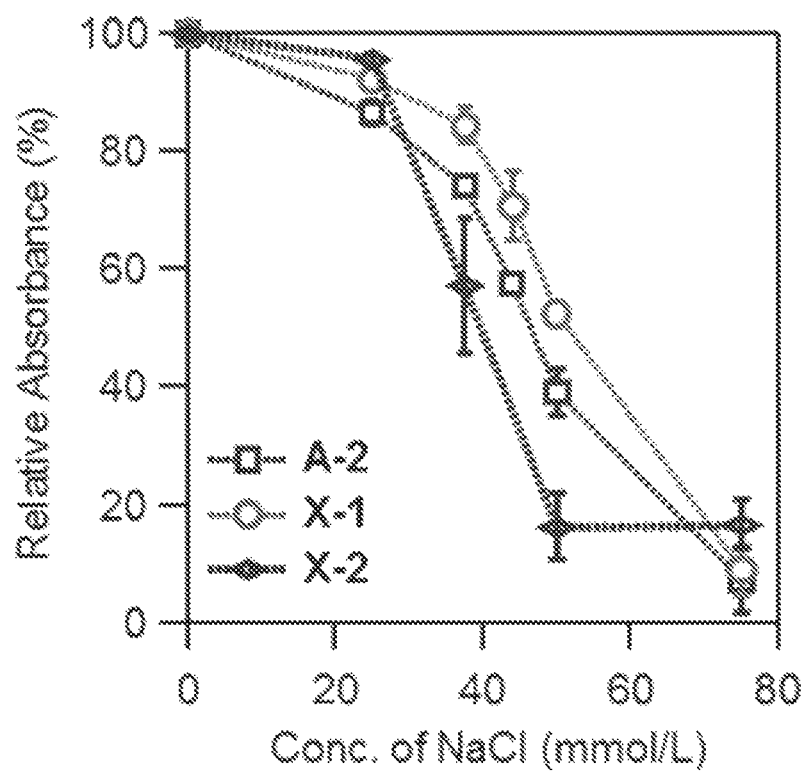
FIG. 1 is a graph showing the results of a salt tolerance evaluation test of modified silver nanoparticles.

Hereinafter, preferred embodiments of the present invention will be described.

The modified metal nanoparticle according to the present embodiment comprises a metal nanoparticle and a cyclic polyether modifying the metal nanoparticle. The modified metal nanoparticle according to the present embodiment can also be referred to as a metal nanoparticle modified with a cyclic polyether.

Since the modified metal nanoparticle according to the present embodiment is high in salt tolerance, it is excellent in vivo stability and can be suitably used as a pharmaceutical composition. Further, since the modified metal nanoparticle according to the present embodiment is also excellent in heat resistance, it can be suitably used particularly for applications requiring heat resistance, such as therapeutic agents (photothermal therapeutic agents) utilizing a photothermal effect.

It has recently been confirmed that cancer cells are weaker against heat than normal cells and begin to necrotize at 41° C. or higher. Since the modified metal nanoparticle according to the present embodiment (in particular, modified gold (Au) nanoparticle) is heat resistant to temperatures of 41° C. or higher, it can be suitably used as a photothermal therapeutic agent for the purpose of removing cancer cells and tumors caused therefrom.

The metal nanoparticle is a nano-sized (1 to 1000 nm) metal particle. The metal nanoparticle may be composed of one metal, or may include two or more metals. The metal nanoparticle may be composed of, for example, gold, silver, iron oxide, titanium oxide, or a complex thereof. From the perspective of remarkably obtaining the effects described above, it is preferable that the metal nanoparticle be a gold nanoparticle or a silver nanoparticle, and it is more preferable that the metal nanoparticle be a gold nanoparticle.

For example, the gold nanoparticle refers to a nanoparticle including gold as a main component, and may be a nanoparticle composed of gold or may be a nanoparticle including gold and another metal. Here, another metal may be, for example, silver, iron oxide, or titanium oxide. The content of the gold in the gold nanoparticle is preferably 80% by mass or more, more preferably 90% by mass or more, further preferably 95% by mass or more, and may be 99% by mass or more, or may be 100% by mass.

The silver nanoparticle refers to a nanoparticle including silver as a main component, and may be a nanoparticle composed of silver or may be a nanoparticle including silver and another metal. Here, another metal may be, for example, gold, iron oxide, or titanium oxide. The content of the silver in the silver nanoparticle is preferably 80%/o by mass or more, more preferably 90% by mass or more, further preferably 95% by mass or more, and may be 99% by mass or more, or may be 100% by mass.

The average particle size of the metal nanoparticle may be, for example, 1 nm or more, preferably 3 nm or more, more preferably 10 nm or more, and may be 14 nm or more. Further, the average particle size of the metal nanoparticle may be, for example, 1000 nm or less, preferably 500 nm or less, more preferably 200 nm or less, further preferably 100 nm or less, and may be 52 nm or less. When the average particle size of the metal nanoparticle is in the above range, a modified metal nanoparticle can be used more suitably as a pharmaceutical composition. In the present specification, the average particle size of the metal nanoparticle refers to a value measured by a light scattering method.

As the cyclic polyether, a cyclic polyalkylene oxide is preferable. Examples of the cyclic polyalkylene oxide include a cyclic polyethylene oxide, a cyclic propylene oxide, a cyclic polyethylene oxide-propylene oxide block copolymer, and among these, from the perspective that the effects are more remarkably exhibited, a cyclic polyethylene oxide is preferable.

The cyclic polyether may have a molecular weight distribution. The number average molecular weight Mn of the cyclic polyether may be, for example, 500 or more, preferably 1000 or more, and more preferably 2000 or more. Further, the number average molecular weight Mn of the cyclic polyether may be, for example, 20000 or less, preferably 10000 or less, and more preferably 6000 or less.

The molecular weight distribution of the cyclic polyether (the ratio of the weight average molecular weight to the number average molecular weight, Mw/Mn) may be, for example, 2 or less, preferably 1.5 or less, and more preferably 1.1 or less. The lower limit of the molecular weight distribution is 1, and in the present embodiment, the molecular weight distribution of the cyclic polyether may be 1.

In the modified metal nanoparticle according to the present embodiment, the mass ratio of the cyclic polyether to the metal nanoparticle (cyclic polyether/metal nanoparticle) is not particularly limited, and may be appropriately changed depending on the type of the metal nanoparticle and the required characteristics.

In a preferred mode, the metal nanoparticle is a gold nanoparticle. In this case, the mass ratio of the cyclic polyether to the gold nanoparticle (cyclic polyether/gold nanoparticle) may be, for example, 50 or more, preferably 100 or more, and more preferably 150 or more. Further, the mass ratio may be, for example, 1500 or less, preferably 1000 or less, and more preferably 700 or less. With such a mass ratio, the above-mentioned effects are more remarkably exhibited. When the metal nanoparticle is a gold nanoparticle, the average particle size of the gold nanoparticle is preferably 50 nm or less, more preferably 40 nm or less, and further preferably 30 nm or less from the perspective of obtaining significantly higher salt tolerance.

In another preferred mode, the metal nanoparticle is a silver nanoparticle. In this case, the mass ratio of the cyclic polyether to the silver nanoparticle (cyclic polyether/silver nanoparticle) may be, for example, 0.1 or more, preferably 0.5 or more, and more preferably 0.9 or more. Further, the mass ratio may be, for example, 50 or less, preferably 30 or less, and more preferably 20 or less. With such a mass ratio, the above-mentioned effects are more remarkably exhibited.

The modified metal nanoparticle according to the present embodiment may be in the form of a dispersion dispersed in a dispersion medium. The dispersion medium may be any dispersion medium capable of dispersing the modified metal nanoparticle, and may be, for example, water, physiological saline, alcohol.

The method for producing the modified metal nanoparticle is not particularly limited. Examples of the method for producing the modified metal nanoparticle include the following Production Methods A and B.

(Production Method A)

Production Method A is a method comprising: a first step of reducing a metal compound in a reaction solution to obtain a first dispersion in which a metal nanoparticle is dispersed; and a second step of adding a cyclic polyether to the first dispersion to obtain a second dispersion in which a modified metal nanoparticle is dispersed.

In the first step, the metal compound serving as the supply source of the metal constituting the metal nanoparticle is reduced in the reaction solution. The metal compound is not particularly limited as long as it is a compound capable of forming a metal nanoparticle by reduction. For example, when a gold nanoparticle is produced as the metal nanoparticle, tetrachloroauric acid or the like can be suitably used as the gold compound. In the case of producing a silver nanoparticle as metal nanoparticle, silver nitrate, silver chloride, or the like can be suitably used as the silver compound.

The solvent of the reaction solution is not particularly limited as long as it is a solvent that does not inhibit the reduction reaction of the metal compound, and for example, may be water, dimethylformamide, ethylene glycol, and toluene, and water is preferable.

The reducing agent is not particularly limited as long as it is a reducing agent capable of reducing the metal compound. Examples of the reducing agent include maltose, sodium citrate, ascorbic acid, sodium borohydride, and glucose.

In the first step, a dispersant may be added to the reaction solution such that the metal formed by the reduction reaction forms a nanoparticle. Examples of the dispersant include polyether, polyvinyl alcohol, polyvinyl pyrrolidone, sodium citrate, and alkanethiol.

In the second step, a modified metal nanoparticle is formed by adding the cyclic polyether to the first dispersion to modify the metal nanoparticle with the cyclic polyether. The addition method is not particularly limited, and a predetermined amount may be added to the reaction solution all at once, or may be added little by little.

(Production Method B)

Production Method B is a method comprising a step of reducing a metal compound in a reaction solution including a cyclic polyether to obtain a dispersion in which a modified metal nanoparticle is dispersed.

In this production method, the modified metal nanoparticle is formed in one step by reducing the metal compound serving as the supply source of the metal constituting the metal nanoparticle in a reaction solution including the cyclic polyether.

Examples of the metal compound, the solvent, and the reducing agent used in Production Method B include the same compounds as the metal compound, solvent, and reducing agent used in Production Method A.

In Production Method B, the dispersants mentioned as examples for Production Method A may be added to the reaction solution.

The modified metal nanoparticle according to the present embodiment can be suitably used as a pharmaceutical composition. Examples of a pharmaceutical composition comprising the modified metal nanoparticle include a radiosensitizer, a photothermal therapeutic agent, and an MRI contrast agent. In addition to these, the modified metal nanoparticle can also be used for applications such as catalysts, sensors, and conductive materials.

Although preferred embodiments of the present invention have been described above, the present invention is not limited to the above-described embodiments.

EXAMPLES

The present invention will now be described in more detail with reference to Examples below, but the present invention is not limited to the Examples.

<Synthesis of Cyclic Polyether>

Synthesis Example 1

The cyclic polyether (PEO (1)) of Synthesis Example 1 was obtained by slowly adding dropwise a solution of a linear polyether (number average molecular weight Mn: 2000 Da) (5.0 g) having a hydroxyl group at both ends and tosyl chloride (0.64 g) in dry THF (100 mL) to a dispersion of KOH (3.3 g) dispersed in a mixed solvent of THF (75 mL) and n-heptane (25 mL), and reacting the resultant mixture at 40° C. for 6 days. The peak top molecular weight Mp of the obtained cyclic polyether determined by size exclusion chromatography was 2000 Da, and Mw/Mn was 1.10.

Synthesis Example 2

The cyclic polyether (PEO (2)) of Synthesis Example 2 was obtained by slowly adding dropwise a solution of a linear polyether (number average molecular weight Mn: 3000 Da) (2.5 g) having a hydroxyl group at both ends and tosyl chloride (0.24 g) in dry THF (50 mL) to a dispersion of KOH (3.3 g) dispersed in a mixed solvent of THF (75 mL) and n-heptane (25 mL), and reacting the resultant mixture at 40° C. for 6 days. The peak top molecular weight Mp of the obtained cyclic polyether determined by size exclusion chromatography was 3200 Da, and Mw/Mn was 1.06.

Synthesis Example 3

The cyclic polyether (PEO (3)) of Synthesis Example 3 was obtained by slowly adding dropwise a solution of a linear polyether (number average molecular weight Mn: 10000 Da) (5.0 g) having a hydroxyl group at both ends and tosyl chloride (0.21 g) in dry THF (100 mL) to a dispersion of KOH (3.3 g) dispersed in a mixed solvent of THF (75 mL) and n-heptane (25 mL), and reacting the resultant mixture at 40° C. for 6 days. The peak top molecular weight Mp of the obtained cyclic polyether determined by size exclusion chromatography was 10500 Da, and Mw/Mn was 1.03.

<Preparation of Modified Metal Nanoparticle>

Example A-1: Preparation of Modified Silver Nanoparticle (A-1)

A modified silver nanoparticle (A-1) was prepared using the PEO (1) synthesized in Synthesis Example 1.

Specifically, the modified silver nanoparticle (A-1) was obtained by reacting PEO (1) (50 mg), silver nitrate (17.4 mg), aqueous ammonia solution (34 µL), NaOH (40 mg), and maltose monohydrate (360 mg) in water (100 mL) at 25° C. for 12 hours. The average particle size of the modified silver nanoparticle (A-1) was 45 nm.

Example A-2: Preparation of Modified Silver Nanoparticle (A-2)

A modified silver nanoparticle (A-2) was prepared using the PEO (2) synthesized in Synthesis Example 2.

Specifically, the modified silver nanoparticle (A-2) was obtained by reacting PEO (2) (50 mg), silver nitrate (17.4 mg), aqueous ammonia solution (34 µL), NaOH (40 mg), and maltose monohydrate (360 mg) in water (100 mL) at 25° C. for 12 hours. The average particle size of the modified silver nanoparticle (A-2) was 31 nm.

Example A-3: Preparation of Modified Silver Nanoparticle (A-3)

A modified silver nanoparticle (A-3) was prepared using the PEO (3) synthesized in Synthesis Example 3.

Specifically, the modified silver nanoparticle (A-3) was obtained by reacting PEO (3) (50 mg), silver nitrate (17.4 mg), aqueous ammonia solution (34 µL), NaOH (40 mg), and maltose monohydrate (360 mg) in water (100 mL) at 25° C. for 12 hours. The average particle size of the modified silver nanoparticle (A-3) was 35 nm.

Comparative Example X-1: Preparation of Modified Silver Nanoparticle (X-1)

A modified silver nanoparticle (X-1) was prepared using linear polyethylene oxide.

Specifically, the modified silver nanoparticle (X-1) was obtained by reacting linear polyethylene oxide (50 mg) having a number average molecular weight Mn of about 4000 Da, silver nitrate (17.4 mg), aqueous ammonia solution (34 µL), NaOH (40 mg), and maltose monohydrate (360 mg) in water (100 mL) at 25° C. for 12 hours. The average particle size of the modified silver nanoparticle (X-1) was 36 nm.

Comparative Example X-2: Preparation of Modified Silver Nanoparticle (X-2)

A modified silver nanoparticle (X-2) was prepared using linear polyethylene oxide dimethyl ether.

Specifically, the modified silver nanoparticle (X-2) was obtained by reacting linear polyethylene oxide dimethyl ether (50 mg) having a number average molecular weight Mn of about 4000 Da, silver nitrate (17.4 mg), aqueous ammonia solution (34 µL), NaOH (40 mg), and maltose monohydrate (360 mg) in water (100 mL) at 25° C. for 12 hours. The average particle size of the modified silver nanoparticle (X-2) was 44 nm.

The modified silver nanoparticles obtained in Example A-2, Comparative Example X-1, and Comparative Example X-2 were evaluated for their salt tolerance by the following method.

(Salt Tolerance Evaluation Test)

Modified silver nanoparticles were added to NaCl solutions at various concentrations (25 mM, 37.5 mM, 44 mM, 50 mM, and 75 mM) to prepare test samples. Regarding test samples after 3 hours had elapsed and test samples after one week had elapsed, the maximum absorption wavelength was measured by ultraviolet-visible spectroscopy. The rate of decrease in absorption at the maximum absorption wavelength (absorption when initial absorption is taken as 100%) was calculated and graphed. The results are shown in FIG. 1.

Example B-1: Preparation of Modified Gold Nanoparticle (B-1)

A modified gold nanoparticle (B-1) was prepared using the PEO (1) synthesized in Synthesis Example 1.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (B-1) was obtained by adding water (100 μL) and PEO (1) (12.5 mg) to the gold nanoparticle solution (400 μL) and reacting the resultant mixture at 25° C. for 10 minutes. The average particle size of the modified gold nanoparticle (B-1) was 14 nm.

Example B-2: Preparation of Modified Gold Nanoparticle (B-2)

A modified gold nanoparticle (B-2) was prepared using the PEO (2) synthesized in Synthesis Example 2.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (B-2) was obtained by adding water (100 μL) and PEO (2) (12.5 mg) to the gold nanoparticle solution (400 μL) and reacting the resultant mixture at 25° C. for 10 minutes. The average particle size of the modified gold nanoparticle (B-2) was 14 nm.

Example B-3: Preparation of Modified Gold Nanoparticle (B-3)

A modified gold nanoparticle (B-3) was prepared using the PEO (3) synthesized in Synthesis Example 3.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (B-3) was obtained by adding water (100 μL) and PEO (3) (12.5 mg) to the gold nanoparticle solution (400 μL) and reacting the resultant mixture at 25° C. for 10 minutes. The average particle size of the modified gold nanoparticle (B-3) was 14 nm.

Comparative Example Y-1: Preparation of Modified Gold Nanoparticle (Y-1)

A modified gold nanoparticle (Y-1) was prepared using linear polyethylene oxide.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (Y-1) was obtained by adding water (100 μL) and linear polyethylene oxide having a number average molecular weight Mn of 2000 Da (12.5 mg) to the gold nanoparticle solution (400 μL) and reacting the resultant mixture at 25° C. for 10 minutes. The average particle size of the modified gold nanoparticle (Y-1) was 14 nm.

Comparative Example Y-2: Preparation of Modified Gold Nanoparticle (Y-2)

A modified gold nanoparticle (Y-2) was prepared using linear polyethylene oxide.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (Y-2) was obtained by adding water (100 μL) and linear polyethylene oxide having a number average molecular weight Mn of 4000 Da (12.5 mg) to the gold nanoparticle solution (400 μL) and reacting the resultant mixture at 25° C. for 10 minutes. The average particle size of the modified gold nanoparticle (Y-2) was 14 nm.

Comparative Example Y-3: Preparation of Modified Gold Nanoparticle (Y-3)

A modified gold nanoparticle (Y-3) was prepared using linear polyethylene oxide.

Specifically, a gold nanoparticle was synthesized by mixing an aqueous solution of $HAuCl_4$ (1.0 mM, 40 mL) and an aqueous solution of sodium citrate (4.0 mM, 39 mL) and refluxing the resultant mixture for 10 minutes. Next, the modified gold nanoparticle (Y-3) was obtained by adding water (100 μL) and linear polyethylene oxide having number average molecular weight Mn of 6000 Da (12.5 mg) to the gold nanoparticle solution (400 μL) and reacting the resultant mixture at 25° C. for 10 minutes. The average particle size of the modified gold nanoparticle (Y-3) was 14 nm.

The modified gold nanoparticles obtained in the Examples and Comparative Examples were evaluated for their salt tolerance by the following method.

(Salt Tolerance Evaluation Test)

Modified gold nanoparticles were added to NaCl solutions at various concentrations (45 mM, 90 mM, 120 mM, and 180 mM) to prepare test samples. Regarding test samples after 3 hours had elapsed, the maximum absorption wavelength was measured by ultraviolet-visible spectroscopy. Cases in which the measured maximum absorption wavelength hardly changed (less than 5 nm) from the initial maximum absorption wavelength were evaluated as A, cases in which the change was less than 15 nm were evaluated as B, cases in which the change was 15 nm or more were evaluated as C, and cases in which the peak widened and measurement of the maximum absorption wavelength became difficult were evaluated as D. The results are shown in Table 1. In addition, for the cases in which the evaluation results were B and C, the amount of change is shown in parentheses in Table 1.

TABLE 1

|  | NaCl concentration (mM) | | | |
| --- | --- | --- | --- | --- |
|  | 45 | 90 | 120 | 180 |
| Example B-1 | B (11 nm) | — | — | — |
| Example B-2 | A | A | A | A |
| Example B-3 | A | A | A | A |
| Comparative Example Y-1 | C (>100 nm) | — | — | — |

TABLE 1-continued

| | NaCl concentration (mM) | | | |
|---|---|---|---|---|
| | 45 | 90 | 120 | 180 |
| Comparative Example Y-2 | D | — | — | — |
| Comparative Example Y-3 | D | — | — | — |

Example C-1: Preparation of Modified Gold Nanoparticle (C-1)

A modified gold nanoparticle (C-1) was prepared using a gold nanoparticle having an average particle size of 10 nm and the PEO (2) synthesized in Synthesis Example 2.

Specifically, 0.54 mL of an aqueous dispersion of the gold nanoparticle (content of the gold nanoparticle being 0.05 mg/mL, average particle size of the gold nanoparticle being 10 nm, manufactured by nanoComposix) was prepared in which 1.5 mg of the PEO (2) was dissolved. The resultant mixture was reacted at 25° C. for 10 minutes and the aqueous dispersion including the modified gold nanoparticle (C-1) was obtained.

Examples C-2 to C-6: Preparations of Modified Gold Nanoparticles (C-2) to (C-6)

Modified gold nanoparticles were prepared in similar manners to Example C-1, except that the average particle sizes of the gold nanoparticles were changed to 15 nm (Example C-2), 20 nm (Example C-3), 30 nm (Example C-4), 40 nm (Example C-5), or 50 nm (Example C-6).

The modified gold nanoparticles (C-1) to (C-6) of Examples C-1 to C-6 were evaluated for their salt tolerance by the following method.

(Salt Tolerance Evaluation Test)

Figure 2:
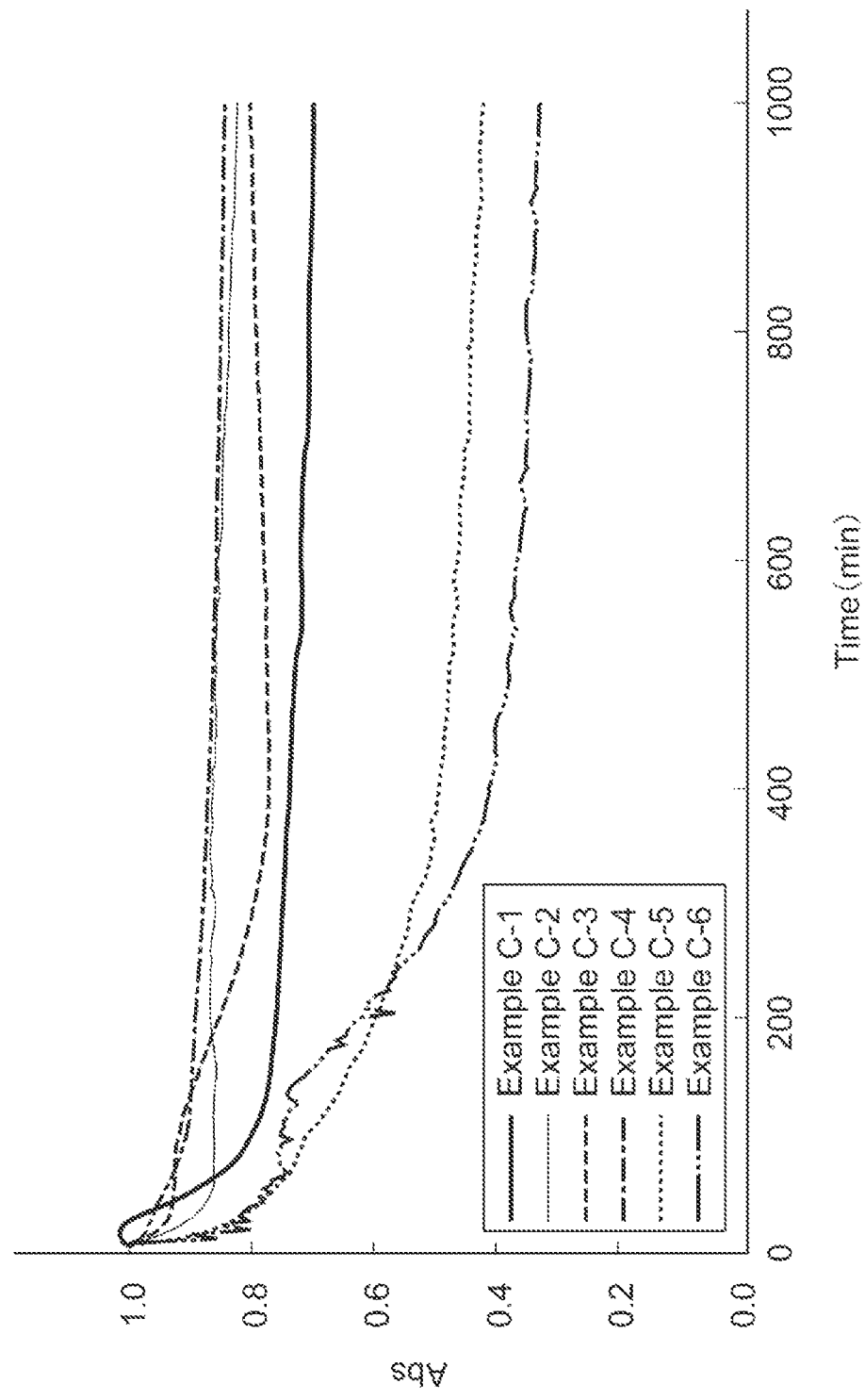
FIG. 2 is a graph showing the results of a salt tolerance evaluation test of modified gold nanoparticles of Examples C-1 to C-6.

A phosphate-buffered saline (PBS, pH 7.4, NaCl concentration: 1500 mM) was added in an amount of 0.06 mL to the aqueous dispersions including the modified gold nanoparticle to prepare test samples. Changes in absorbance over time of the test samples were measured at 37° C. by an ultraviolet-visible near-infrared spectrophotometer manufactured by JASCO Corporation. FIG. 2 is a graph in which the ordinate represents relative absorbance with respect to absorbance at the start of measurement and the abscissa represents elapsed time.

Example D-1: Preparation of Modified Gold Nanoparticle (D-1)

A modified gold nanoparticle (D-1) was prepared using a gold nanoparticle having an average particle size of 10 nm and the PEO (1) synthesized in Synthesis Example 1.

Specifically, 0.54 mL of an aqueous dispersion of the gold nanoparticle (content of the gold nanoparticle being 0.05 mg/mL, average particle size of the gold nanoparticle being 10 nm, manufactured by nanoComposix) was prepared in which 1.5 mg of the PEO (1) was dissolved. The resultant mixture was reacted at 25° C. for 10 minutes and the aqueous dispersion including the modified gold nanoparticle (D-1) was obtained.

Examples D-2 and D-3: Preparations of Modified Gold Nanoparticles (D-2) and (D-3)

Modified gold nanoparticles were prepared in similar manners to Example D-1, except that the average particle sizes of the gold nanoparticles were changed to 30 nm (Example D-2) or 50 nm (Example D-3).

The modified gold nanoparticles (D-1) to (D-3) of Examples D-1 to D-3 were evaluated for their salt tolerance by the following method.

(Salt Tolerance Evaluation Test)

Figure 3:
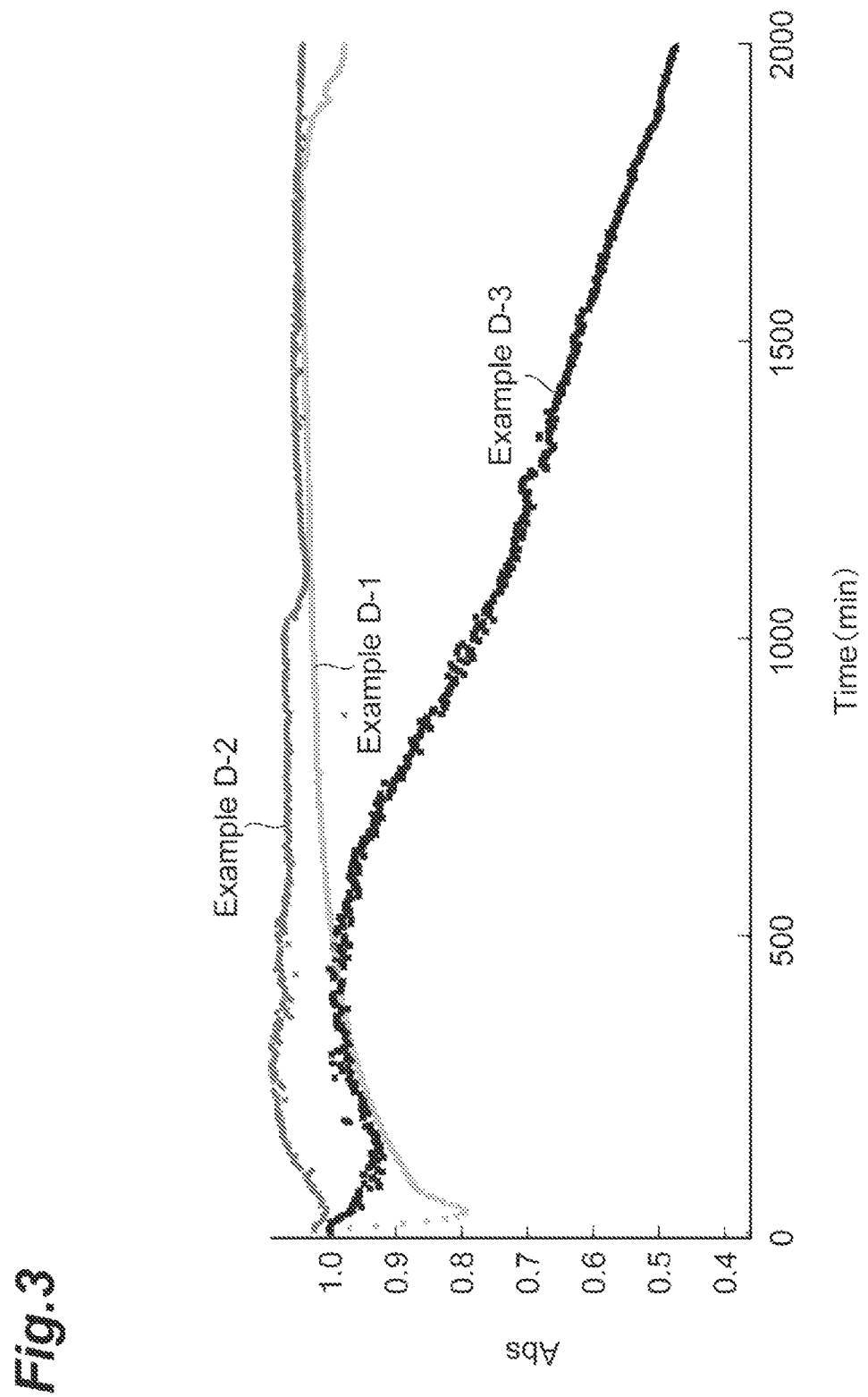
FIG. 3 is a graph showing the results of a salt tolerance evaluation test of modified gold nanoparticles of Examples D-1 to D-3.

A phosphate-buffered saline (PBS, pH 7.4, NaCl concentration: 1500 mM) was added in an amount of 0.06 mL to the aqueous dispersions including the modified gold nanoparticle to prepare test samples. Changes in absorbance over time of the test samples were measured at 45° C. by an ultraviolet-visible near-infrared spectrophotometer manufactured by JASCO Corporation. FIG. 3 is a graph in which the ordinate represents relative absorbance with respect to absorbance at the start of measurement and the abscissa represents elapsed time.

What is claimed is:

1. A modified metal nanoparticle, comprising:
   a metal nanoparticle; and
   a cyclic polyether modifying the metal nanoparticle,
   wherein a number average molecular weight of the cyclic polyether is 500 to 20000.

2. The modified metal nanoparticle according to claim 1, wherein the metal nanoparticle is a gold nanoparticle or a silver nanoparticle.

3. The modified metal nanoparticle according to claim 1, wherein an average particle size of the metal nanoparticle is 1 to 1000 nm.

4. The modified metal nanoparticle according to claim 1, wherein the cyclic polyether is a cyclic polyethylene oxide.

5. A modified metal nanoparticle, comprising:
   a metal nanoparticle; and
   a cyclic polyether modifying the metal nanoparticle,
   wherein the metal nanoparticle is a gold nanoparticle, and
   a mass ratio of the cyclic polyether to the gold nanoparticle is 50 to 1500.

6. The modified metal nanoparticle according to claim 5, wherein an average particle size of the metal nanoparticle is 1 to 1000 nm.

7. The modified metal nanoparticle according to claim 5, wherein the cyclic polyether is a cyclic polyethylene oxide.

8. The modified metal nanoparticle according to claim 5, wherein a number average molecular weight of the cyclic polyether is 500 to 20000.

9. A modified metal nanoparticle, comprising:
   a metal nanoparticle; and
   a cyclic polyether modifying the metal nanoparticle,
   wherein the metal nanoparticle is a silver nanoparticle, and a mass ratio of the cyclic polyether to the silver nanoparticle is 0.1 to 50.

10. The modified metal nanoparticle according to claim 9, wherein an average particle size of the metal nanoparticle is 1 to 1000 nm.

11. The modified metal nanoparticle according to claim 9, wherein the cyclic polyether is a cyclic polyethylene oxide.

12. The modified metal nanoparticle according to claim 9, wherein a number average molecular weight of the cyclic polyether is 500 to 20000.

13. A pharmaceutical composition comprising a modified metal nanoparticle,
    wherein the modified metal nanoparticle comprises:
    a metal nanoparticle; and
    a cyclic polyether modifying the metal nanoparticle.

14. The pharmaceutical composition according to claim 13, wherein the pharmaceutical composition is a radiosensitizer, a photothermal therapeutic agent, or an MRI contrast agent.

15. The pharmaceutical composition according to claim 13, wherein the metal nanoparticle is a gold nanoparticle or a silver nanoparticle.

16. The pharmaceutical composition according to claim 13, wherein an average particle size of the metal nanoparticle is 1 to 1000 nm.

17. The pharmaceutical composition according to claim 13, wherein the cyclic polyether is a cyclic polyethylene oxide.

18. The pharmaceutical composition according to claim 13, wherein a number average molecular weight of the cyclic polyether is 500 to 20000.

19. The pharmaceutical composition according to claim 13, wherein the metal nanoparticle is a gold nanoparticle, and a mass ratio of the cyclic polyether to the gold nanoparticle is 50 to 1500.

20. The pharmaceutical composition according to claim 13, wherein the metal nanoparticle is a silver nanoparticle, and a mass ratio of the cyclic polyether to the silver nanoparticle is 0.1 to 50.

* * * * *